United States Patent [19]

Mardis et al.

[11] 4,434,076
[45] * Feb. 28, 1984

[54] CLAY CATION COMPLEXES AND THEIR USE TO INCREASE VISCOSITY OF LIQUID ORGANIC SYSTEMS

[75] Inventors: Wilbur S. Mardis, Trenton, N.J.; Claude M. Finlayson, Houston, Tex.

[73] Assignee: NL Industries, Inc., New York, N.Y.

[ * ] Notice: The portion of the term of this patent subsequent to Jul. 5, 2000 has been disclaimed.

[21] Appl. No.: 313,034

[22] Filed: Oct. 19, 1981

[51] Int. Cl.$^3$ .............................................. B01J 13/00
[52] U.S. Cl. .................................. 252/315.2; 106/27; 106/38.7; 106/287.17; 252/8.5 M; 252/8.55 R; 252/28; 252/DIG. 8; 260/448 C; 524/236
[58] Field of Search .................... 260/448 C; 252/316, 252/28, 315.2; 106/287.17

[56] References Cited

U.S. PATENT DOCUMENTS

| | | | |
|---|---|---|---|
| 2,033,856 | 3/1936 | Smith | 546/10 |
| 2,531,427 | 11/1950 | Hauser | 260/448 C |
| 2,531,440 | 11/1950 | Jordan | 252/28 |
| 2,548,679 | 4/1951 | Olin | 564/285 |
| 2,658,869 | 11/1953 | Stross et al. | 252/28 |
| 2,767,177 | 10/1956 | Erickson | 260/242 |
| 2,859,234 | 11/1958 | Clem | 260/448 |
| 3,461,163 | 8/1969 | Boothe | 564/296 |
| 3,472,740 | 10/1969 | Boothe | 203/47 |
| 3,537,994 | 11/1970 | House | 252/13 |
| 3,929,849 | 12/1975 | Oswald | 260/448 C |
| 3,945,836 | 3/1976 | Miyata | 106/22 |
| 3,974,125 | 8/1976 | Oswald et al. | 523/216 |
| 4,054,537 | 10/1977 | Wright et al. | 423/331 |
| 4,097,437 | 6/1978 | Dhake | 524/236 |
| 4,116,866 | 9/1978 | Finlayson | 252/315.2 |
| 4,317,737 | 3/1982 | Oswald et al. | 252/28 |

FOREIGN PATENT DOCUMENTS

| | | | |
|---|---|---|---|
| 1106281 | 3/1968 | United Kingdom | 252/316 |
| 1592271 | 7/1981 | United Kingdom . | |

OTHER PUBLICATIONS

The Condensed Chemical Dictionary, 9th Edition, Revised by Hawley, Van Nostrand Reinhold Co., (1977), pp. 630, 636.

H. Van Olphen: "An Introduction to Clay Colloid Chemistry," 2nd Ed., John Wiley & Sons, New York, London, Sydney, Toronto (1963), p. 64.

"Industrial Minerals and Rocks," 4th Ed., S. J. Lefond, Ed., *American Institute of Mining*, Metallurgical and Petroleum Engineers, Inc., New York, N.Y. (1975), pp. 1244–1247.

R. E. Grim: "Clay Mineralogy," 2nd Ed., McGraw Hill Book Co., New York, St. Louis, San Francisco, Toronto, London, Sydney (1968), pp. 77–79.

*Primary Examiner*—Richard D. Lovering

[57] ABSTRACT

An organophilic clay gellant comprising the reaction product of an organic cationic compound and a smectite-type clay having a cation exchange capacity of at least 75 milliequivalents per 100 grams of said clay, wheein said organic cationic compound contains (a) a first member selected from the group consisting of a $\beta$, $\gamma$-unsaturated alkyl group, and a hydroxyalkyl group having 2 to 6 carbon atoms, and mixtures thereof, (b) a second member comprising a long chain alkyl group having 12 to 60 carbon atoms and (c) a third and fourth alkyl member.

13 Claims, No Drawings

CLAY CATION COMPLEXES AND THEIR USE TO INCREASE VISCOSITY OF LIQUID ORGANIC SYSTEMS

This invention relates to organophilic organic-clay complexes which are dispersible in organic liquids to form a gel therein. Depending on the composition of the gel, such gels may be useful in lubricating greases, oil base muds, oil base packer fluids, paint-varnish-lacquer removers, paints, foundry molding sand binders, adhesives and sealants, inks, polyester laminating resins, polyester gel coats, and the like.

It is well known that the organic compounds which contain a cation will react under favorable conditions by ion-exchange with clays which contain a negative layer-lattice and exchangeable cations to form organophilic organic-clay products. If the organic cation contains at least one alkyl group containing at least 10 carbon atoms, then such organoclays have the property of swelling in certain organic liquids. See for Example U.S. Pat. No. 2,531,427, and U.S. Pat. No. 2,966,506, both incorporated herein by reference, and the book "Clay Mineralogy", 2nd Edition, 1968 by Ralph E. Grim (McGraw Hill Book Co., Inc.), particularly Chapter 10, Clay-Mineral-Organic Reactions; pp. 356–368 of Ionic Reactions, Smectite; and pp. 392–401 of Organophilic Clay-Mineral Complexes.

Since the commercial introduction of organoclays in the early 1950's, it has become well known that maximum gelling (thickening) efficiency from these organoclays is achieved by adding a low molecular weight polar organic material to the composition. Such polar organic materials have been variously called dispersants, dispersion aids, solvating agents, dispersion agents and the like. See for example the following U.S. Pat. Nos.: O'Hallaran 2,677,661; McCarthy et al. 2,704,276; Stratton 2,833,720; Stratton 2,879,229; Stansfield et al. 3,294,683. The use of such dispersion aids was found unnecessary when using specially designed organophilic clays derived from substituted quaternary ammonium compounds. See U.S. Pat. Nos.: Finlayson et al. 4,105,578 and Finlayson 4,208,218.

The most efficient and accepted polar materials for use as dispersants have been found to be low molecular weight alcohols and ketones, particularly methanol and acetone. These dispersants, however, have very low flash points and require the use of flameproof apparatus. Higher boiling, high flash point dispersants may be used but these are less efficient and often produce gels having poor secondary properties such as mechanical stability, poor thickening or storage stability.

Most of the organophilic clays heretofore produced have exhibited limited broad range gelling utilities resulting predominantly from fluctuating dispersion and viscosity properties. While the materials disclosed by Finlayson et al in U.S. Pat. No. 4,105,578 have not shown such deficiencies, these materials are produced with relative difficulty and added cost resulting from the selection of benzyl starting materials.

Accordingly, there is a need for an organophilic clay gellant which is easy and yet cost effective to prepare and which can be readily dispersed in organic systems without requiring the essential presence of a polar dispersant, other than perhaps minor quantities of water, for gelling organic systems.

An organophilic clay gellant having enhanced dispersibility in non-aqueous fluid systems has been unexpectedly discovered when prepared as the reaction product of a smectite clay and an organic cationic compound having at least one long chain alkyl group and at least one group selected from a $\beta,\gamma$-unsaturated alkyl group or a hydroxyalkyl group having 2 to 6 carbon atoms.

In particular, an organophilic clay gellant has been unexpectedly discovered which comprises the reaction product of an organic cationic compound and a smectite-type clay having a cation exchange capacity of at least 75 milliequivalents per 100 grams of said clay, wherein said organic cationic compound contains (a) a first member selected from the group consisting of a $\beta$, $\gamma$-unsaturated alkyl group, and a hydroxyalkyl group having 2 to 6 carbon atoms, and mixtures thereof, (b) a second member comprising a long chain alkyl group having 12 to 60 carbon atoms and (c) a third and fourth member selected from a member of group (a) above, an aralkyl group, and an alkyl group having 1 to 22 carbon atoms and mixtures thereof; and wherein the amount of said organic cationic compound is from 90 to 140 milliequivalents per 100 grams of said clay, 100% active clay basis.

In addition, the invention involves a method of increasing the viscosity of a liquid organic system in the absence of a polar organic dispersant comprising mixing with said liquid organic system an amount sufficient to effect said viscosity increase of organophilic clay gellant, which comprises the reaction product of an organic cationic compound and a smectite-type clay having a cation exchange capacity of at least 75 milliequivalents per 100 grams of said clay, wherein said organic cationic compound contains (a) a first member selected from the group consisting of a $\beta$, $\gamma$-unsaturated alkyl group, and a hydroxyalkyl group having 2 to 6 carbon atoms, and mixtures thereof, (b) a second group comprising a long chain alkyl group having 12 to 60 carbon atoms and (c) a third and fourth member selected from a member of a group (a), an aralkyl group, and an alkyl group having 1 to 22 carbon atoms and a mixture thereof; and wherein the amount of said organic cationic compound is from 90 to 140 milliequivalents per 100 grams of said clay, 100% active clay basis.

The clays used to prepare the organophilic clay gellants of this invention are smectite-type clays which have a cation exchange capacity of at least 75 milliequivalents per 100 grams of clay. Particularly desirable types of clay are the naturally-occurring Wyoming variety of swelling bentonite and like clays, and hectorite, a swelling magnesium-lithium silicate clay.

The cation exchange capacity of the smectite-type clays can be determined by the well-known ammonium acetate method.

The clays, especially the bentonite type clays, are preferably converted to the sodium form if they are not already in this form. This can conveniently be done by preparing an aqueous clay slurry and passing the slurry through a bed of cation exchange resin in the sodium form. Alternatively, the clay can be mixed with water and a soluble sodium compound such as sodium carbonate, sodium hydroxide and the like, followed by shearing the mixture with a pugmill or extruder.

Smectite-type clays prepared naturally or synthetically by either a pneumatolytic or, preferably a hydrothermal synthesis process can also be used to prepare the present organophilic clays. Representative of such clays are montmorillonite, bentonite, beidellite, hectorite, saponite, and stevensite. Synthetic clays may be synthesized hydrothermally by forming an aqueous reaction mixture in the form of a slurry containing mixed hydrous oxides or hydroxides of the desired metal with or without, as the case may be, sodium (or alternate exchangeable cation or mixtures thereof) fluoride in the proportions for the particular synthetic smectite desired. The slurry is then placed in an autoclave and heated under autogenous pressure to a temperature within the range of approximately 100° to 325° C., preferably 274° to 300° C., for a sufficient period of time to form the desired product.

The organic cationic compounds which are useful in this invention may be selected from a wide range of materials that are capable of forming an organophilic clay by exchange of cations with the smectite-type clay. The organic cationic compound must have a positive charge localized on a single atom or on a small group of atoms within the compound. Preferably the organic cation is selected from the group consisting of quaternary ammonium salts, phosphonium salts, and mixtures thereof, as well as equivalent salts, and wherein the organic cation contains at least one member selected from (a) a $\beta$, $\gamma$-unsaturated alkyl group and/or a hydroxyalkyl group having 2 to 6 carbon atoms and (b) a long chain alkyl group. The remaining moieties on the central positive atom are chosen from a member from group (a) above or an aralkyl group and/or an alkyl group having from 1 to 22 carbon atoms.

The $\beta$, $\gamma$-unsaturated alkyl group may be selected from a wide range of materials. These compounds may be cyclic or acyclic, unsubstituted or substituted with aliphatic radicals containing up to 3 carbon atoms such that the total number of aliphatic carbons in the $\beta$, $\gamma$-unsaturated radical is 6 or less. The $\beta$, $\gamma$-unsaturated alkyl radical may be substituted with an aromatic ring that likewise is conjugated with the unsaturation of the $\beta$, $\gamma$ moiety or the $\beta$, $\gamma$-radical is substituted with both aliphatic radicals and aromatic rings.

Representative examples of cyclic $\beta$, $\gamma$-unsaturated alkyl groups include 2-cyclohexenyl and 2-cyclopentenyl. Representative examples of acyclic $\beta$, $\gamma$-unsaturated alkyl groups containing 6 or less carbon atoms include propargyl; allyl (2-propenyl); crotyl (2-butenyl); 2-pentenyl; 2-hexenyl; 3-methyl-2-butenyl; 3-methyl-2-pentenyl; 2,3-dimethyl-2-butenyl; 1,1-dimethyl-2-propenyl; 1,2-dimethyl propenyl; 2,4-pentadienyl; and 2,4-hexadienyl. Representative examples of acyclic-aromatic substituted compounds include cinnamyl (3-phenyl-2-propenyl); 2-phenyl-2-propenyl; and 3-(4 methoxyphenyl)-2-propenyl. Representative examples of aromatic and aliphatic substituted materials include 3-phenyl-2-cyclohexenyl; 3-phenyl-2-cyclopentenyl; 1,1-dimethyl-3-phenyl-2-propenyl; 1,1,2-trimethyl-3-phenyl-2-propenyl; 2,3-dimethyl-3-phenyl-2-propenyl; 3,3-dimethyl-2-phenyl-2-propenyl; and 3-phenyl-2-butenyl.

The hydroxyalkyl group is selected from a hydroxyl substituted aliphatic radical wherein the hydroxyl is not substituted at the carbon adjacent to the positively charged atom, and the group has from 2 to 6 aliphatic carbons. The alkyl group may be substituted with an aromatic ring independently from the 2 to 6 aliphatic carbons. Representative examples include 2-hydroxyethyl (ethanol); 3-hydroxypropyl; 4-hydroxypentyl; 6-hydroxyhexyl; 2-hydroxypropyl (isopropanol); 2-hydroxybutyl; 2-hydroxypentyl; 2-hydroxyhexyl; 2-hydroxycyclohexyl; 3-hydroxycyclohexyl; 4-hydroxycyclohexyl; 2-hydroxycyclopentyl; 3-hydroxycyclopentyl; 2-methyl-2-hydroxypropyl; 1,1,2-trimethyl-2-hydroxypropyl; 2-phenyl-2-hydroxyethyl; 3-methyl-2-hydroxybutyl; and 5-hydroxy-2-pentenyl.

The long chain alkyl radicals may be branched or unbranched, saturated or unsaturated, substituted or unsubstituted and should have from 12 to 60 carbon atoms in the straight chain portion of the radical.

The long chain alkyl radicals may be derived from natural occurring oils including various vegetable oils, such as corn oil, coconut oil, soybean oil, cottonseed oil, castor oil and the like, as well as various animal oils or fats such as tallow oil. The alkyl radicals may likewise be petrochemically derived such as from alpha olefins.

Representative examples of useful branched, saturated radicals include 12-methylstearyl; and 12-ethylstearyl. Representative examples of useful branched, unsaturated radicals include 12-methyloleyl and 12-ethyloleyl. Representative examples of unbranched saturated radicals include lauryl; stearyl; tridecyl; myristyl (tetradecyl); pentadecyl; hexadecyl; hydrogenated tallow, docosonyl. Representative examples of unbranched, unsaturated and unsubstituted radicals include oleyl, linoleyl; linolenyl, soya and tallow.

The remaining groups on the positively charged atom are chosen from (a) a member of the group selected from a $\beta$, $\gamma$-unsaturated alkyl group and a hydroxyalkyl group having 2 to 6 carbon atoms, both described above; (b) an alkyl group having 1 to 22 carbon atoms, cyclic and acyclic and (c) an aralkyl group, that is benzyl and substituted benzyl moieties including fused ring moieties having lineal or branched 1 to 22 carbon atoms in the alkyl portion of the structure.

Representative examples of an aralkyl group, that is benzyl and substituted benzyl moieties, would include benzyl and those materials derived from e.g. benzyl halides, benzhydryl halides, trityl halides, $\alpha$-halo $\alpha$-phenylalkanes wherein the alkyl chain has from 1 to 22 carbon atoms such as 1-halo-1-phenylethane; 1-halo-1-phenyl propane; and 1-halo-1-phenyloctadecane; substituted benzyl moieties such as would be derived from ortho-, meta-, and para-chlorobenzyl halides, para-methoxybenzyl halides; ortho-, meta- and para-nitrilobenzyl halides, and ortho-, meta- and para-alkylbenzyl halides wherein the alkyl chain contains from 1 to 22 carbon atoms; and fused ring benzyltype moieties such as would be derived from 2-halomethylnaphthalene, 9-halomethylanthracene and 9-halomethylphenanthrene, wherein the halo group would be defined as chloro, bromo, iodo, or any other such group which serves as a leaving group in the nucleophilic attack of the benzyl type moiety such that the nucleophile replaces the leaving group on the benzyl type moiety.

Representative examples of useful alkyl groups which may be lineal and branched, cyclic and acyclic include methyl; ethyl; propyl; 2-propyl; iso-butyl; cyclopentyl; and cyclohexyl.

The alkyl radicals may also be derived from other natural oils, both substituted and unsubstituted such as those described above, including various vegetable oils, such as tallow oil, corn oil, soybean oil, cottonseed oil, castor oil, and the like, as well as various animal oils and fats.

Many processes are known to prepare organic cationic salts. For example, when preparing a quaternary ammonium salt one skilled in the art would prepare a dialkyl secondary amine, for example, by the hydrogenation of nitriles, see U.S. Pat. No. 2,355,356; and then form the methyl dialkyl tertiary amine by reductive alkylation using formaldehyde as the source of methyl radical. Also see Shapiro et al. U.S. Pat. No. 3,136,819 for forming the quaternary amine halide by adding benzyl chloride or benzyl bromide to the tertiary amine as well as Shapiro et al. U.S. Pat. No. 2,775,617.

The salt anion is preferably selected from the group consisting of chloride and bromide, and mixtures thereof, and is more preferably chloride, although other anions such as acetate, hydroxide, nitrite, etc., may be present in the organic cationic compound to neutralize the cation. A representative formula being

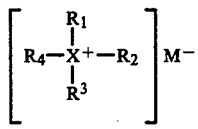

wherein $R_1$ is selected from the group consisting of a $\beta$, $\gamma$-unsaturated alkyl group and a hydroxyalkyl group having 2 to 6 carbon atoms and mixtures thereof; $R_2$ is a long chain alkyl group having 12 to 60 carbon atoms; $R_3$ and $R_4$ are selected from a group consisting of an $R_1$ group, an aralkyl group, and an alkyl group having from 1 to 22 carbon atoms; X is phosphorous or nitrogen; and where $M^-$ is selected from the group consisting of $Cl^-$, $Br^-$, $I^-$, $NO_2^-$, $OH^-$ and $C_2H_3O_2^-$.

The organophilic clays of this invention can be prepared by admixing the clay, quaternary ammonium compound and water together, preferably at a temperature within the range from 20° C. to 100° C., and most preferably from 35° C. to 77° C. for a period of time sufficient for the organic compound to coat the clay particles, followed by filtering, washing, drying and grinding. In using the organophilic clays in emulsions, the drying and grinding steps may be eliminated. When admixing the clay, quaternary ammonium compound and water together in such concentrations that a slurry is not formed, then the filtration and washing steps can be eliminated.

The clay is preferably dispersed in water at a concentration from about 1 to 80% and preferably 2% to 7%, the slurry optionally centrifuged to remove non-clay impurities which constitute about 10% to about 50% of the starting clay composition, the slurry agitated and heated to a temperature in the range from 35° C. to 77° C. The quaternary amine salt is then added in the desired milliequivalent ratio, preferably as a liquid in isopropanol or dispersed in water and the agitation continued to effect the reaction.

For convenience of handling it is preferred that the total organic content of the organophilic clay reaction products of this invention should be less than about 50% by weight of the organoclay. While higher amounts are usable the reaction product is difficult to filter, dry and grind.

The amount of organic cation added to the clay for purposes of this invention must be sufficient to impart to the clay the enhanced dispersion characteristic desired. This amount is defined as the milliequivalent ratio which is the number of milliequivalents (M.E.) of the organic cation in the organoclay per 100 grams of clay, 100% active clay basis. The organophilic clays of this invention must have a milliequivalent ratio from 90 to 140 and preferably 100 to 130. At lower milliequivalent ratios the organophilic clays produced are not effective gellants even though they may be good gellants when dispersed in a conventional manner with polar organic dispersants. At higher milliequivalent ratios the organophilic clays are poor gellants. However, it will be recognized that the preferred milliequivalent ratio within the range from 90 to 140, will vary depending on the characteristics of the organic system to be gelled by the organophilic clay.

The manner in which the organic cation functions in the organophilic clay reaction products of this invention is not fully known. The unique properties associated with the compositions of this invention are believed however to relate to the electron withdrawing and donating portions of the cation and particularly to the essential presence of at least one long chain alkyl group coupled with a $\beta$, $\gamma$-unsaturated alkyl group and/or a hydroxyalkyl group. When bonded to a positively charged atom the long chain alkyl group appears to function as an electron donator which aids in delocalizing the positive charge. More importantly however it enables the clay platelets to be separated sufficiently to allow further separation under moderate shear conditions. In contrast, the $\beta$, $\gamma$-unsaturated alkyl group appears to create a delocalization of the positive charge which may result from a resonance and/or inductive effect occurring with the unsaturated alkyl group. This effect does not occur to any significant extent with other prior art saturated alkyl groups. The enhanced function of the short chain hydroxyalkyl group appears to be related to the internal covalent bonded polar activating moiety, namely the hydroxyl group when not adjacent to the positively charged atom. This effect is negated when the hydroxyl moiety is located on a carbon atom adjacent to the positive charged atom or on an alkyl aliphatic carbon greater than 6 carbon atoms long.

The compositions of the invention as discussed above find wide utility as rheological additives in non-aqueous fluid systems generally. The non-aqueous fluid compositions in which the self activating organophilic clays are useful include paints, varnishes, enamels, waxes, epoxies, mastics, adhesives, cosmetics, inks, polyester laminating resins, polyester gel coats, and the like. These fluids may be prepared by any conventional method such as described in U.S. Pat. No. 4,208,218 including colloid mills, roller mills, ball mills, and high speed dispersers, in which the pigment materials become well dispersed in the organic vehicle by the high shear used in processing.

The organophilic clay gellant is employed in such compositions in amounts sufficient to obtain the desired rheological properties such as high viscosity at low shear rates, control of sagging of fluid films and prevention of settling and hard packing of pigments present in the non-aqueous fluid compositions. Amounts of the organophilic clay gellant employed in the non-aqueous fluid system should preferably be between about 0.1% an about 15% based on the weight of the treated non-aqueous fluid system and preferably between 0.3% and 5.0% to yield the desired rheological effects.

The following examples are given to illustrate the invention, but are not deemed to be limiting thereof. All percentages given throughout the specification are based upon weight unless otherwise indicated.

The smectite-type clays used in the Examples were hectorite and Wyoming bentonite. The hectorite clay was slurried in water and centrifuged to remove essentially all of the non-clay impurities. The Wyoming betonite clay was slurried in water, centrifuged to remove essentially all of the non-clay impurities, and ion-exchanged to the sodium form by passing the slurry through a bed of cation exchange resin in the sodium form.

Examples 1 to 17 demonstrate the preparation of various organic cationic compounds which compounds may be used as reactants with an organoclay to form the organophilic clay reaction products of this invention.

The organic cationic compounds of the invention were prepared by standard prior art methods starting with an amine having the desired number of long chain alkyl groups bonded to the nitrogen atom. This long chain alkyl amine was then reacted by reductive alkylation with an aldehyde and/or by nucleophilic displacement of an alkyl halide to form the desired quaternary ammonium compound.

The organic cationic compounds exemplified are representative of the cations of the invention and are not intended to be inclusive of only operative compounds.

EXAMPLE 1

Allyl ethanol di(hydrogenated-tallow) ammonium chloride (abbreviated AE2HT).

Placed 852.9 gm. ethanol di(hydrogenated-tallow) amine, 130.7 gm. allyl chloride, 18.1 gm. allyl bromide (as a catalyst), 13 gm. sodium bicarbonate and approximately 400 ml. isopropyl alcohol as solvent in a 2-liter autoclave. The temperature was kept at 100° C. and the mixture was allowed to react overnight. An aliquot was removed, filtered, and analyzed using HCl and NaOH. There was 4.2% amine and 1.2% amine HCl. Added 5 gm. sodium bicarbonate to neutralize the amine HCl. The autoclave was sealed and the temperature was allowed to rise to 120° C. Methyl chloride was introduced and was added periodically until the pressure remained constant (65 psig) for one hour. At this point, the reaction was considered complete. The final analyses showed an Effective gram molecular weight (MW) of 966.97.

EXAMPLE 2

Allyl methyl di(hydrogenated-tallow) ammonium chloride (abbreviated AM2HT).

Placed 824.7 gm. methyl di(hydrogenated-tallow) amine, approximately 350 ml. isopropyl alcohol, 250 gm. NaHCO$_3$, 191.3 gm. allyl chloride, and 10 gm. allyl bromide (as a catalyst) in a 4-liter reaction vessel equipped with a condenser and mechanical stirrer. Heated and allowed mixture to reflux gently. A sample was removed, filtered, and titrated with HCl and NaOH. The reaction was considered complete as there was 0.0% amine HCl and 1.8% amine. The final analysis showed an Effective gram molecular weight of 831.17.

EXAMPLE 3

Allyl benzyl di(hydrogenated-tallow) ammonium chloride (abbreviated AB2HT).

This reaction involved two steps—formation of the tertiary amine and preparation of the quaternary ammonium chloride.

Placed 759.3 gm. di(hydrogenated-tallow) amine, 168.0 gm. sodium bicarbonate, and approximately 400 ml. isopropyl alcohol in a 4-liter reaction vessel equipped with a condenser, mechanical stirrer, thermometer and addition funnel. Heated mixture until amine dissolved to 50° C. Added 153.1 gm. allyl chloride dropwise over a period of one hour at 50° C. After approximately two hours of reacting at 50° C., two samples were removed and filtered and one was reacted with phenyl isocyanate. Both were then titrated with HCl. An additional 153.1 grams allyl chloride was added dropwise to the reaction mixture. Allowed mixture to reflux one hour before sampling again. This time the reaction was considered complete. The excess allyl chloride was distilled off.

208.9 gm. of benzyl chloride was placed in a 4-liter vessel containing the above reaction mixture. The mixture was heated and allowed to reflux for 4 days. A sample was removed, filtered and analyzed. It was found to contain 0.18% amine HCl and 10.75% amine. 25 gm. benzyl chloride and an additional 50 gm. NaHCO$_3$ were added and refluxing for two days. Analyses of a sample showed there to be 10.17% amine and 0.0% amine HCl. The reaction mixture was placed in a 1-liter autoclave, heated to 100° C., and charged with methyl chloride. When the pressure did not drop after the incremental introduction of MeCl, the reaction was complete. A sample was removed, filtered and analyzed. There was still 2.86% amine present, but reaction was considered complete at this time. Final analysis showed an Effective gram molecular weight of 1423.17.

EXAMPLE 4

Allyl benzyl ethanol di(hydrogenated-tallow) ammonium chloride (abbreviated ABEHT)

A 2-liter autoclave was charged with benzyl ethanol hydrogenated-tallow amine (632.2 gm.; 1.5 mol), 133.9 gm. allyl chloride, 18.1 gm. allyl bromide, 160 gm. sodium bicarbonate, and 175 ml isopropyl alcohol. The mixture was allowed to react at 100° C. overnight. An aliquot was removed and found to contain 61.2% amine. The apparent slow reaction rate was due to a leak in the autoclave. When the problem was corrected, an additional 133.9 gm. of allyl chloride and 18.1 gm. allyl bromide was added. The reaction as allowed to go overnight. An aliquot was removed and analyzed. It contained 16.1% amine and 0.4% amine HCl. An additional 36 gm. of allyl bromide was added. The following day, a sample was removed, analyzed, and found to contain 7% amine and 0.5% amine HCl. Allyl bromide (15 gm.) and 25 gm. of sodium bicarbonate were added and the reaction was continued overnight. Analyses of an aliquot showed there to be 0.0% amine HCl and 5.2% amine. The autoclave was charged with methyl chloride to finish the quaternization reaction. Final analysis showed an Effective gram molecular weight of 780.7.

EXAMPLE 5

Allyl benzyl methyl hydrogenated-tallow ammonium chloride (abbreviated ABMHT)

A 2-liter autoclave was charged with 436.8 gm. (1.17 mol) benzyl methyl hydrogenated tallow amine, 133.9 gm. (1.75 mol) allyl chloride, 14.5 gm. (0.12 mol) allyl bromide, 150 gm. sodium bicarbonate and 150 ml isopropyl alcohol. The mixture was allowed to react at 100° C. overnight. An aliquot was removed, analyzed and found to contain about 10.8% amine and 0.07% amine HCl. An additional 30 gm of allyl chloride was added. The mixture was allowed to continue reacting overnight. A second aliquot was removed, filtered and analyzed. It contained 22.8% amine and 0.0% amine HCl. The increase in % amine was probably due to the presence of amine carbonate. Therefore, the reaction mixture was filtered and 10 gm. sodium hydroxide in 10 ml. of water was added. An additional 30 gm. of allyl bromide was added and the mixture was allowed to continue reacting a 100° C. overnight. Analyses of an aliquot showed there to be 3.0% amine, and 1.3% sodium bicarbonate (30 gm.) was added and the quaternization was finished using methyl chloride. An aliquot was removed and analyzed. It contained 0.0% amine HCl and 2.8% amine. The mixture was stirred with about 50 gm. sodium bicarbonate and the reaction was considered complete. Final analyses showed an Effective gram MW of 826.09.

EXAMPLE 6

Allyl diethanol octadecyl ammonium chloride (abbreviated A2EAlk.).

A 2-liter autoclave was charged with 755.6 gm. (2.1 mol) diethanol octadecyl amine, 191.3 gm. (2.5 mol) allyl chloride, 12.7 gm. (0.105 mol) of allyl bromide, 390 ml. isopropyl alcohol, and 20.8 gm. sodium bicarbonate. The mixture was allowed to react overnight at 100° C. An aliquot was removed, filtered and analyzed. It was found to contain 3.3% amine HCl and 0.5% amine. An additional 20.0 gm. sodium bicarbonate and 20 gm. allyl chloride was added and the mixture was allowed to continue reacting at 100° C. The reaction was considered complete the following day. The final analysis showed an Effective gram MW of 656.49.

EXAMPLE 7

Allyl dimethyl octadecyl ammonium chloride (abbreviated A2MAlk.).

A 2-liter reaction vessel equipped with a mechanical stirrer and a reflux condenser was charged with 660.0 gm. dimethyl octadecyl amine, 199.0 gm. (2.19 mol) allyl chloride, 13.3 (0.11 mol) gm. allyl bromide, 20 gm. sodium bicarbonate, and 350 ml. isopropyl alcohol. This mixture was heated under reflux overnight. Analyses of a filtered aliquot indicated the reaction was complete. The mixture was filtered and upon analysis had an Effective gram MW of 496.74.

EXAMPLE 8

Diallyl methyl hydrogenated-tallow ammonium chloride (abbreviated 2AMHT).

A 2-liter reaction vessel equipped with a reflux condenser, mechanical stirrer, and addition funnel was charged with 403.5 gm. (1.5 mol) hydrogenated-tallow amine, 112.0 gm. sodium hydroxide, 42.0 gm. sodium bicarbonate, and 275 ml isopropyl alcohol. The mixture was heated until the amine dissolved. Allyl chloride (252.6 gm.; 3.3 mol) was added dropwise over approximately 1½ hours. After allowing the reaction mixture to reflux gently for 22 hours an aliquot was removed and filtered. One portion of the aliquot was reacted with phenylisocyanate and both were titrated with 0.100 Normal HCl. The results indicated that there was about 75% tertiary amine. The reaction mixture was allowed to continue refluxing for an additional 2 hours before it was analyzed again. Titration results at that time showed there to be approximately 90% tertiary amine. The excess allyl chloride was distilled off.

The above reaction mixture was placed in a 2-liter autoclave and reacted with methyl chloride. An aliquot was removed, filtered, and analyzed. There was 0.0% amine HCl and 0.67% amine present. The reaction mixture was filtered and upon analysis had an Effective gram molecular weight of 635.34.

EXAMPLE 9

Diallyl di(hydrogenated-tallow) ammonium chloride (abbreviated 2A2HT).

A 4-liter reaction vessel equipped with reflux condenser, mechanical stirrer and addition funnel was charged with 746.0 gm. di(hydrogenated-tallow) amine, 400 ml. isopropyl alcohol, and 175 gm. sodium bicarbonate. The mixture was heated until the amine dissolved. Allyl chloride (344.4 gm; 4.5 mol) was added dropwise over a period of 1.5 hours. The rate of addition and temperature were controlled to maintain a gentle reflux.

After 4 days, an aliquot was removed, filtered and analyzed. The reaction was 38.9% complete (61.1% amine; 0.011% amine HCl). An additional 250 gm. allyl chloride was added dropwise and the mixture was allowed to continue refluxing gently overnight. Another aliquot was removed and found to contain 9.79% amine and 0.56% amine HCl. An additional 100 gm. allyl chloride was added. The following day, analysis showed there to be 3.4% amine and 0.34% amine HCl. The addition of 100 gm. allyl chloride did not cause the reaction to progress any further. The reaction mixture was filtered and cooled to room temperature. Methyl iodide was added to finish the quaternization. The final analysis showed an Effective gram MW of 1111.5, amine 0.397% and amine HCl 0.0%.

EXAMPLE 10

Triallyl hydrogenated-tallow ammonium chloride (abbreviated 3AHT).

A 2-liter autoclave was charged with 392.1 gm (1.5 mol) hydrogenated-tallow amine, 355.9 gm. allyl chloride, 18.2 gm. allyl bromide, 120 gm. sodium hydroxide, 84 gm. sodium bicarbonate and 200 ml. isopropyl alcohol. The mixture was allowed to react at 100° C. overnight. An aliquot was removed, filtered and analyzed. It was found to contain about 10% amine and 0.2% amine HCl. An additional 56.2 gm. allyl bromide was added and the mixture was allowed to continue reacting at 100° C. An aliquot was removed the following day. Analyses showed there to be 1.97 amine and 3.4% amine HCl.

The reaction mixture was filtered. Sodium bicarbonate (10 gm.) was added and the mixture was stirred for about ½ hour. The mixture was filtered and 12.0 gm. of methyl iodide was added to finish the quaternization.

Analysis showed an Effective gram MW of 841.10.

EXAMPLE 11

Ethanol dimethyl octadecyl ammonium chloride (abbreviated E2M Alk).

Dimethyl octadecyl amine (779.35 gm.; 2.6 mol); 257.63 gm. (3.2 mol) 2-chloroethanol, and approximately 400 ml. of isopropanol were placed in a 4-liter reaction vessel equipped with a mechanical stirrer and a reflux condenser. The mixture was stirred at room temperature for approximately 2 weeks. Analyses showed there to be 67% amine and 0.7% amine HCl. The mixture was heated under reflux for one week. An aliquot was removed, analyzed, and found to contain 0.0% amine and 2.8% amine HCl. Sodium bicarbonate (67 gm) was added and the mixture was allowed to continue refluxing. The following day, an aliquot was analyzed and contained 2.9% amine. The reaction mixture was filtered and cooled before iodomethane was added to finish the reaction. The final analyses showed amine 1.23%; amine HCl 0.409%; and effective gram MW 567.9.

EXAMPLE 12

Ethanol benzyl methyl hydrogenated-tallow ammonium chloride (abbreviated EBMHT).

A 2-liter autoclave was charged with 632.2 gm. (1.5 mol) benzyl ethanol hydrogenated-tallow amine, 160 gm. sodium bicarbonate, and 175 ml. isopropyl alcohol. The temperature was allowed to rise to 100° C. Methyl chloride was introduced and was added periodically until the pressure remained constant for one hour. An aliquot was removed and analyzed. It was found to contain 18.4% amine and 3.0% amine HCl. The autoclave was recharged with methyl chloride and heated at 100° C. overnight. A second aliquot was removed, filtered, analyzed and found to contain 4.8% amine and 3.2% amine HCl. The reaction mixture was filtered, stirred with more sodium bicarbonate and refiltered. It was recrystallized twice from acetone. The final analyses showed amine 0.33%; amine HCl 0.29%; and an Effective gram MW of 393.9.

EXAMPLE 13

Ethanol benzyl di(hydrogenated-tallow) ammonium chloride (abbreviated EB2HT).

Ethanol di(hydrogenated-tallow) amine (823.7 gm., 1.5 mol), 215.2 gm. benzyl chloride (1.7 mol), 25.7 gm. benzyl bromide (0.15 mol), 15.0 gm. sodium bicarbonate, and 430 ml. isopropyl alcohol were placed in a 2-liter flask equipped with mechanical stirrer and reflux condenser. This mixture was heated under reflux.

After 2 days, an aliquot was removed, filtered and analyzed. It was found to contain 3.9% amine and 5.6% amine HCl. An additional 20.0 gm. sodium bicarbonate was added, and the reaction mixture was transferred to a 2-liter autoclave. The quaternization was finished with methyl chloride. The standard procedure of methylation was used except that the temperature was kept ≦80° C. The reaction went to completion. The final analyses showed an Effective gram MW of 941.1.

EXAMPLE 14

Diethanol benzyl octadecyl Ammonium chloride (abbreviated 2EB Alk).

A 4-liter reaction vessel equipped with a reflux condenser and mechanical stirrer was charged with 719.6 gm. (2.0 mol) diethanol octadecylamine, 278.5 gm. (2.2 mol) benzyl chloride, 20 gm. of sodium bicarbonate and approximately 400 ml. isopropyl alcohol. The reaction mixture was heated under reflux overnight. An aliquot was removed, analyzed and found to contain 7.4% amine and 1.7% amine HCl. The mixture was allowed to continue reacting overnight. A second aliquot was analyzed and found to contain 4.1% amine and 3.7% amine HCl. An additional 20 gm. of sodium bicarbonate and 30 gm. benzyl chloride were added. After one week the reaction had not progressed any further. The mixture was placed in the autoclave and the quaternization was finished with methyl chloride. The final analyses showed amine 0.0%; amine HCl <1% and Effective gram MW 834.4.

EXAMPLE 15

Diethanol methyl octadecyl ammonium chloride (abbreviated 2EM Alk).

A 2-liter autoclave was charged with 858.3 gm. (2.4 mol) diethanol octadecyl amine, 20 gm. sodium bicarbonate and 420 ml. isopropyl alcohol. The temperature was raised to 100° C. Methyl chloride was introduced and was added periodically until the pressure remained constant (65 psig) for one hour.

An aliquot was removed and filtered. The analyses showed there to be 2.67% amine. The reaction mixture was filtered and 18.0 gm. iodomethane was added to finish the quaternization. The final analyses showed 1.64% amine and 0.0% amine HCl; and Effective gram MW of 725.27.

EXAMPLE 16

Diethanol di(hydrogenated-tallow) ammonium chloride (abbreviated 2E2HT).

A 4-liter reaction vessel equipped with a condenser and mechanical stirrer was charged with 812.5 gm. ethanol di(hydrogenated-tallow) amine, 144.9 gm. 2-chloroethanol and approximately 500 ml. isopropyl alcohol. This mixture was heated under reflux for 2 weeks.

An aliquot was removed, analyzed and found to contain approximately 47% amine and 12% amine HCl. An additional 100 gm. of 2-chloroethanol was added and the mixture was allowed to continue refluxing. After 5 days, a second aliquot was removed. It was found to contain 21% amine and 10% amine HCl. The amine HCl was neutralized by the addition of 75 gm. of NaHCO₃. The reaction mixture was placed in a 2-liter autoclave and reacted with methyl chloride to finish the quaternization. The final analyses are 0.0% amine; 1.9% amine HCl; and Effective gram MW 1246.55.

EXAMPLE 17

Triethanol octadecyl ammonium chloride (abbreviated 3E Alk).

Placed 175.6 gm. diethanol octadecyl amine, 120.8 gm. 2-chloroethanol, 200 ml. isopropyl alcohol, and a few crystals of potassium bromide (as a catalyst) in a 1-liter flask equipped with a condenser and mechanical stirrer. Heated mixture and allowed to reflux for 10 days.

Analyses were run by titrating a sample with 0.100 Normal HCl (to determine % amine) and with 0.100 Normal NaOH (to determine % amine HCl). After 10 days, the reaction was 10% complete (79.8% amine; 10.2% amine HCl). The reaction was allowed to continue refluxing.

After an additional 10 days, analyses showed there to be 20.22% amine and 29.76% amine HCl. More 2-chloroethanol (48.3 gm., 0.6 mol) was added and the amine HCl was neutralized with 27.7 gm. (0.33 mol) sodium bicarbonate. The mixture was allowed to reflux one more week. At this point there was 4.92% amine HCl and 8.05% amine. The quat was then recrystallized twice from a mixture of acetone and toluene.

The final analyses are as follows: amine 0.32%; amine HCl 1.97%; and Effective gram MW of 452.04.

EXAMPLES 18–67 AND COMPARATIVE A–G

These examples demonstrate the use of preparations of organophilic clays of this invention in various solvent systems. The compositions are set forth in Table I with the solvent compatibility results in Table II.

The organophilic clay reaction products were prepared by charging into a container of suitable size a 3% clay slurry (sodium form of Wyoming bentonite or hectorite) which was heated to 60° C. with stirring. A solution of the organic cationic compound was added to the clay slurry and stirred for a period of time sufficient to complete the reaction (generally 10 to 60 minutes). The organoclay was collected on a vacuum filter. The filter cake was washed with hot (40°-80° C.) water and dried at 60° C. The dried organoclay was ground using a hammer mill or similar grinding apparatus to reduce the particle size and then sieved through a 200-mesh screen prior to use. Amounts of reactants used are set forth in Table 1. Screen size was U.S. Standard mesh.

The enhanced dispersion characteristics of the organophilic clays of this invention is illustrated by the solvent compatibility test. This test shows the results potentially obtainable in utilizing the inventive compositons. The solvent compatibility test is conducted by taking a sample of the organophilic clay which is sifted into 10 milliliters of various solvents contained in separate 10 milliliter graduated cylinders. The organophilic clay is added at such a rate that the particles are wetted evenly and clumping is not permitted to occur. The samples are allowed to equilibrate after all the organophilic clay has been added (approximately 30 minutes). The volume occupied by the organophilic clay is then recorded in tenths of a milliliter; this number is called the swelling volume.

The mixture is vigorously shaken 50 times, 10 times horizontally, 40 times vertically, and allowed to stand overnight. The volume occupied by the organophilic clay is again recorded in tenths of a milliliter; this value is called the settling volume.

The swelling volume gives an indication of the compatibility of the organic portion of the organophilic clay with the solvents tested; the settling volume gives an indication of the ease of dispersion of the organophilic clay in that solvent under low shear conditions.

Because of variances in the rate of sifting of the organoclay into the solvent and the vigor with which the sample is shaken, the numbers are not absolute. Small differences in the volumes are not considered significant. Rather, the values are intended to be for comparison only.

The results indicate that the compositions of this invention have a wide range of dispersibility in a variety of solvent systems and that the inventive materials are more readily dispersible than similar conventional quaternary amine reaction products. The solvent systems employed are representative of three main solvent systems; aliphatic, aromatic and moderately polar. These systems cover a broad range of systems within which the rheological additives of this invention will be used.

TABLE I

| Example No. | Organic Cationic Compound | Type of Clay | Organic Cation ME Ratio |
|---|---|---|---|
| Comparative A | dimethyl-n-propyl HT ammonium | bentonite | 111.1 |
| Comparative B | methyl benzyl 2HT ammonium | bentonite | 112.0 |
| Comparative C | dimethyl 2HT ammonium | bentonite | 95.0 |
| Comparative D | dimethyl 2HT ammonium | hectorite | 95.0 |
| Comparative E | benzyl dimethyl HT ammonium | bentonite | 102.0 |
| Comparative F | benzyl dimethyl HT ammonium | hectorite | 102.0 |
| Comparative G | benzyl 3HT ammonium | bentonite | 114.0 |
| Inventive 18 | allyl methyl 2HT ammonium | bentonite | 109.9 |
| Inventive 19 | propargyl dimethyl HT ammonium | bentonite | 108.7 |
| Inventive 20 | diallyl-N—(1-naphthylmethyl) HT ammonium | bentonite | 110.08 |
| Inventive 21 | p-anisyl diallyl HT ammonium | bentonite | 108.04 |
| Inventive 22 | allyl methyl diphenylmethyl HT ammonium | bentonite | 110.8 |
| Inventive 23 | 3-methyl-2-butenyl dimethyl HT ammonium | bentonite | 119.1 |
| Inventive 24 | cinnamyl dimethyl octadecyl ammonium | bentonite | 108.43 |
| Inventive 25 | 2-hydroxyhexyl dimethyl HT ammonium | bentonite | 109.8 |
| Inventive 26 | 2-hydroxyhexyl dimethyl HT ammonium | bentonite | 110.5 |
| Inventive 27 | 6-hydroxyhexyl dimethyl HT ammonium | bentonite | 111.54 |
| Inventive 28 | di(2-hydroxy-2-phenethyl) methyl HT ammonium | bentonite | 109.52 |
| Inventive 29 | 2-hydroxycyclohexyl dimethyl HT ammonium | bentonite | 108.9 |
| Inventive 30 | cyclohexenyl dimethyl HT ammonium | bentonite | 110.2 |
| Inventive 31 | 2,4-hexadienyl dimethyl HT ammonium | bentonite | 108.57 |
| Inventive 32 | p-anisyl diethanol octadecyl ammonium | bentonite | 109.42 |
| Inventive 33 | bis(2-hydroxyethyl) 1-(napthylmethyl) octadecyl ammonium | bentonite | 110.48 |
| Inventive 34 | bis(2-hydroxyethyl) methyl dicoco ammonium | bentonite | 111.3 |
| Inventive 35 | allyl dimethyl oleyl ammonium | bentonite | 110.6 |
| Inventive 36 | ethanol dimethyl oleyl ammonium | bentonite | 109.7 |
| Inventive 37 | triallyl dodecyl ammonium | bentonite | 110.61 |
| Inventive 38 | diallyl dicoco ammonium | bentonite | 111.45 |
| Inventive 39 | ethanol methyl dicoco ammonium | bentonite | 110.0 |
| Inventive 40 | allyl methyl dicoco ammonium | bentonite | 110.15 |
| Inventive 41 | ethanol dimethyl dodecyl ammonium | bentonite | 111.7 |
| Inventive 42 | diallyl cyclohexyl stearyl ammonium | bentonite | 108.7 |
| Inventive 43 | crotyl dimethyl octadecyl ammonium | bentonite | 111.9 |
| Inventive 44 | allyl tri-n-octadecyl phosphonium | bentonite | 108.87 |
| Inventive 45 | allyl 3HT ammonium | bentonite | 110.8 |
| Inventive 46 | ethanol benzyl 2HT ammonium | bentonite | 110.0 |
| Inventive 47 | ethanol 3HT ammonium | bentonite | 111.8 |
| Inventive 48 | diallyl 2HT ammonium | bentonite | 108.4 |
| Inventive 49 | allyl benzyl 2HT ammonium | bentonite | 110.0 |
| Inventive 50 | allyl ethanol 2HT ammonium | bentonite | 108.8 |
| Inventive 51 | diethanol 2HT ammonium | bentonite | 110.2 |
| Inventive 52 | ethanol methyl 2HT ammonium | bentonite | 106.7 |
| Inventive 53 | ethanol methyl 2HT ammonium | bentonite | 108.2 |

TABLE I-continued

| Example No. | Organic Cationic Compound | Type of Clay | Organic Cation ME Ratio |
|---|---|---|---|
| Inventive 54 | triallyl HT ammonium | bentonite | 111.2 |
| Inventive 55 | diallyl benzyl HT ammonium | bentonite | 110.2 |
| Inventive 56 | diallyl ethanol HT ammonium bentonite | | 108.0 |
| Inventive 57 | allyl dibenzyl HT ammonium | bentonite | 111.8 |
| Inventive 58 | allyl ethanol HT ammonium | bentonite | 108.1 |
| Inventive 59 | allyl dimethyl HT ammonium | bentonite | 110.3 |
| Inventive 60 | allyl benzyl ethanol HT ammonium | bentonite | 109.8 |
| Inventive 61 | allyl benzyl methyl HT ammonium | bentonite | 108.5 |
| Inventive 62 | allyl ethanol methyl HT ammonium | bentonite | 110.7 |
| Inventive 63 | ethanol dibenzyl HT ammonium | bentonite | 111.4 |
| Inventive 64 | diethanol benzyl HT ammonium | bentonite | 111.5 |
| Inventive 65 | ethanol benzyl methyl HT ammonium | bentonite | 109.2 |
| Inventive 66 | diethanol methyl HT ammonium | bentonite | 111.7 |
| Inventive 67 | ethanol dimethyl HT ammonium | bentonite | 108.1 |

"HT" stands for hydrogenated tallow

TABLE II

Solvent Compatibility

| | Toluene | | Methyl isobutyl ketone | | 60/40 Di-isodecyl Phthalate/Toluene | | Heptane | |
|---|---|---|---|---|---|---|---|---|
| Example No. | Swelling Volume | Settling Volume | Swelling Volume | Settling Volume | Swelling Volume | Settling Volume | Swelling Volume | Settling Volume |
| Comparative A | 14 | 20 | 14 | 15 | 14 | 16 | 3 | 3 |
| Comparative B | 13 | 27 | 12 | 14 | 14 | 20 | 11 | 14 |
| Comparative C | 12 | 20 | 14 | 17 | 16 | 24 | 5 | 6 |
| Comparative D | 9 | 11 | 11 | 12 | 13 | 14 | 5 | 4 |
| Comparative E | 13 | 28 | 26 | 42 | 13 | 15 | 2 | 4 |
| Comparative F | 4 | 6 | 14 | 16 | 16 | 18 | 2 | 3 |
| Comparative G | 13 | 62 | 7 | 11 | 7 | 7 | 25 | 100 |
| Inventive 18 | 15 | 88 | 13 | 16 | 16 | 20 | 7 | 11 |
| Inventive 19 | 17 | 22 | 26 | 33 | 23 | 26 | 1 | 1 |
| Inventive 20 | 1 | 1 | 4 | 4 | 2 | 2 | 1 | 1 |
| Inventive 21 | 7 | 9 | 15 | 20 | 12 | 12 | 2 | 2 |
| Inventive 22 | 2 | 3 | 7 | 9 | 7 | 7 | 2 | 3 |
| Inventive 23 | 21 | 38 | 16 | 23 | 17 | 19 | 2 | 2 |
| Inventive 24 | 8 | 10 | 16 | 25 | 8 | 11 | 2 | 2 |
| Inventive 25 | 5 | 7 | 12 | 14 | 10 | 10 | 2 | 3 |
| Inventive 26 | 13 | 18 | 14 | 17 | 12 | 12 | 2 | 4 |
| Inventive 27 | 15 | 26 | 22 | 26 | 16 | 20 | 3 | 3 |
| Inventive 28 | 2 | 4 | 12 | 16 | 5 | 5 | 2 | 4 |
| Inventive 29 | 6 | 8 | 20 | 25 | 12 | 12 | 1 | 1 |
| Inventive 30 | 18 | 30 | 16 | 22 | 16 | 16 | 1 | 1 |
| Inventive 31 | 10 | 10 | 18 | 24 | 12 | 14 | 2 | 2 |
| Inventive 32 | 12 | 17 | 13 | 20 | 13 | 16 | 8 | 8 |
| Inventive 33 | 4 | 4 | 18 | 22 | 8 | 10 | 2 | 3 |
| Inventive 34 | 1 | 1 | 16 | 17 | 3 | 3 | 2 | 2 |
| Inventive 35 | 12 | 16 | 16 | 23 | 12 | 12 | 2 | 2 |
| Inventive 36 | 7 | 6 | 14 | 18 | 8 | 8 | 1 | 1 |
| Inventive 37 | 10 | 12 | 20 | 14 | 12 | 14 | 3 | 4 |
| Inventive 38 | 16 | 50 | 11 | 18 | 10 | 11 | 12 | 17 |
| Inventive 39 | 8 | 10 | 12 | 15 | 10 | 12 | 2 | 4 |
| Inventive 40 | 18 | 28 | 12 | 16 | 11 | 10 | 2 | 4 |
| Inventive 41 | 3 | 4 | 14 | 16 | 8 | 9 | 1 | 1 |
| Inventive 42 | 10 | 10 | 18 | 26 | 12 | 14 | 2 | 2 |
| Inventive 43 | 18 | 33 | 19 | 26 | 18 | 18 | 5 | 5 |
| Inventive 44 | 7 | 12 | 8 | 8 | 7 | 7 | 22 | 69 |
| Inventive 45 | 15 | 65 | 6 | 10 | 8 | 9 | 22 | 84 |
| Inventive 46 | 12 | 24 | 14 | 21 | 11 | 15 | 10 | 16 |
| Inventive 47 | 17 | 56 | 6 | 8 | 10 | 9 | 20 | 56 |
| Inventive 48 | 14 | 33 | 12 | 14 | 12 | 15 | 8 | 10 |
| Inventive 49 | 12 | 16 | 12 | 16 | 10 | 12 | 4 | 6 |
| Inventive 50 | 12 | 20 | 11 | 16 | 10 | 13 | 7 | 9 |
| Inventive 51 | 8 | 10 | 10 | 12 | 10 | 12 | 2 | 5 |
| Inventive 52 | 7 | 12 | 10 | 16 | 10 | 12 | 3 | 3 |
| Inventive 53 | 12 | 18 | 12 | 14 | 11 | 14 | 2 | 3 |
| Inventive 54 | 10 | 18 | 16 | 22 | 12 | 17 | 1 | 3 |
| Inventive 55 | 8 | 10 | 16 | 22 | 12 | 14 | 2 | 2 |
| Inventive 56 | 14 | 22 | 18 | 28 | 18 | 20 | 2 | 2 |
| Inventive 57 | 12 | 20 | 18 | 30 | 16 | 18 | 2 | 2 |
| Inventive 58 | 8 | 8 | 17 | 22 | 10 | 11 | 2 | 3 |
| Inventive 59 | 16 | 30 | 19 | 29 | 18 | 24 | 1 | 3 |
| Inventive 60 | 12 | 17 | 20 | 28 | 15 | 17 | 1 | 2 |
| Inventive 61 | 8 | 10 | 16 | 20 | 10 | 12 | 2 | 1 |
| Inventive 62 | 14 | 18 | 23 | 28 | 14 | 18 | 1 | 2 |

TABLE II-continued

| | Solvent Compatibility Solvent | | | | | | | |
|---|---|---|---|---|---|---|---|---|
| | Toluene | | Methyl isobutyl ketone | | 60/40 Di-isodecyl Phthalate/Toluene | | Heptane | |
| Example No. | Swelling Volume | Settling Volume | Swelling Volume | Settling Volume | Swelling Volume | Settling Volume | Swelling Volume | Settling Volume |
| Inventive 63 | 14 | 29 | 20 | 34 | 14 | 23 | 2 | 2 |
| Inventive 64 | 5 | 5 | 20 | 25 | 7 | 8 | 2 | 2 |
| Inventive 65 | 8 | 12 | 20 | 24 | 8 | 10 | 1 | 1 |
| Inventive 66 | 4 | 4 | 19 | 22 | 5 | 8 | 1 | 1 |
| Inventive 67 | 6 | 8 | 17 | 19 | 8 | 10 | 1 | 2 |

The invention being thus described, it will be obvious that the same may be varied in many ways. Such variations are not to be regarded as a departure from the spirit and scope of the invention and all such modifications are intended to be included within the scope of the following claims.

We claim:

1. An organophilic clay gellant, which comprises: the reaction product of an organic cationic ammonium compound and a smectite-type clay having a cation exchange capacity of at least 75 milliequivalents per 100 grams of said clay, wherein said organic cationic ammonium compound contains
    (a) a first member selected from the group consisting of a α,γ-unsaturated alkyl group having 6 or less aliphatic carbon atoms, a hydroxyalkyl group having 2 to 6 aliphatic carbon atoms, and mixtures thereof,
    (b) a second member comprising a long chain alkyl group having 12 to 60 carbon atoms and
    (c) a third and fourth member selected from a member of group (a), an aralkyl group having 1 to 22 carbon atoms in the alkyl portion, an alkyl group having 1 to 22 carbon atoms and mixtures thereof; and wherein the amount of said organic cationic ammonium compound is from 90 to 140 milliequivalents per 100 grams of said clay, 100% active clay basis.

2. The composition of claim 1 wherein the smectite-type clay is selected from the group consisting of hectorite and sodium bentonite.

3. The composition of claim 1 wherein the β,γ-unsaturated alkyl group is selected from an unsubstituted and substituted group consisting of cyclic groups, acyclic alkyl groups having less than 7 carbon atoms, acyclic alkyl groups substituted with aromatic groups, and aromatic groups substituted with aliphatic groups.

4. The composition of claim 1 wherein the hydroxyalkyl group is selected from substituted and unsubstituted groups consisting of cyclic groups and aliphatic groups having 2 to 6 carbon atoms with the hydroxyl substitution on $C_2$ to $C_6$.

5. The composition of claim 1 wherein the long chain alkyl group of member (b) has from 12 to 22 carbon atoms.

6. The composition of claim 6 wherein the long chain alkyl group is a long chain fatty acid group.

7. The composition of claim 1 wherein the amount of said organic cationic ammonium compound is from 100 to 130 milliequivalents per 100 grams of said clay, 100% active clay basis.

8. An organophilic clay gellant, which comprises: the reaction product of an organic cationic compound and a smectitetype clay having a cation exchange capacity of at least 75 milliequivalents per 100 grams of said clay, wherein said organic cationic compound has the general formula:

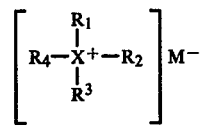

wherein $R_1$ is selected from the group consisting of a α,γ-unsaturated alkyl group having 6 or less aliphatic carbon atoms, a hydroxyalkyl group having 2 to 6 carbon atoms, and mixtures thereof; $R_2$ is a long chain alkyl group having 12 to 60 carbon atoms; $R_3$ and $R_4$ are selected from the group consisting of an $R_1$ group, an aralkyl group having 1 to 22 carbon atoms in the alkyl portion, an alkyl group having from 1 to 22 carbon atoms and mixtures thereof; X is nitrogen; and $M^-$ is selected from the group consisting of $Cl^-$, $I^-$, $Br^-$, $NO_2^-$, $OH^-$ and $C_2H_3O_2^-$, and wherein the amount of said organic cationic compound is from 90 to 140 milliequivalents per 100 grams of said clay, 100% active clay basis.

9. A method of increasing the viscosity of a liquid organic system in the absence of a polar organic dispersant comprising mixing with said liquid organic system an amount sufficient to effect said viscosity increase of an organophilic clay gellant comprising the reaction product of an organic cationic ammonium compound and a smectite-type clay having a cation exchange capacity of at least 75 milliequivalents per 100 grams of said clay, wherein said organic ammonium cationic compound contains
    (a) a first member selected from the group consisting of a α,γ-unsaturated alkyl group having 6 or less aliphatic carbon atoms, a hydroxyalkyl group having 2 to 6 aliphatic atoms, and mixtures thereof,
    (b) a second member comprising a long chain alkyl group having 12 to 60 carbon atoms, and
    (c) a third and fourth member selected from a member of group (a), an aralkyl group having 1 to 22 carbon atoms in the alkyl portion, an alkyl group having 1 to 22 cerbon atoms and mixtures thereof; and wherein the amount of said organic cationic ammonium compound is from 90 to 140 milliequivalents per 100 grams of said clay, 100% active clay basis.

10. The method of claim 9 wherein the smectite-type clay is selected from the group consisting of hectorite and sodium bentonite.

11. The method of claim 9 wherein the β,γ-unsaturated alkyl group is selected from an unsubstituted and substituted group consisting of cyclic groups, acyclic alkyl groups having less than 7 carbon atoms, acyclic alkyl groups substituted with aromatic groups, and aromatic groups substituted with aliphatic groups.

12. The method of claim 9 wherein the hydroxyalkyl group is selected from substituted and unsubstituted groups consisting of cyclic groups and aliphatic groups having 2 to 6 carbon atoms with the hydroxyl substitution on $C_2$ to $C_6$.

13. The method of claim 9 wherein the long chain alkyl group of member (b) has from 12 to 22 carbon atoms.

* * * * *

UNITED STATES PATENT AND TRADEMARK OFFICE
CERTIFICATE OF CORRECTION

PATENT NO. : 4,434,076
DATED : February 28, 1984
INVENTOR(S) : Wilbur S. Mardis and Claude Malcolm Finlayson It is certified that error appears in the above-identified patent and that said Letters Patent is hereby corrected as shown below:

In column 17, line 28; column 18, line 25; and column 18, line 49, "$\alpha,\gamma$" should read --$\beta,\gamma$--.

In column 17, line 59, "claim 6" should read --claim 5--.

In column 17, line 67, "smectitetype" should read --smectite-type--.

Signed and Sealed this

Twenty-fourth Day of July 1984

[SEAL]

Attest:

Attesting Officer

GERALD J. MOSSINGHOFF
Commissioner of Patents and Trademarks